United States Patent [19]

Barner et al.

[11] 4,204,995

[45] May 27, 1980

[54] CHOLESTANE DERIVATIVES

[75] Inventors: Richard Barner, Witterswil; Joseph Hübscher, Seon, both of Switzerland

[73] Assignee: Hoffmann-La Roche Inc., Nutley, N.J.

[21] Appl. No.: 15,021

[22] Filed: Feb. 26, 1979

[30] Foreign Application Priority Data

Mar. 15, 1978 [CH] Switzerland .................. 2818/78

[51] Int. Cl.$^2$ ............................................. C07J 17/00
[52] U.S. Cl. ........................ 260/239.55 C; 260/397.2
[58] Field of Search ............ 260/239.55 D, 239.55 C; /Steroids MS File

[56] References Cited

U.S. PATENT DOCUMENTS

| 4,105,660 | 8/1978 | Jones ................................ 260/397.2 |
| 4,145,346 | 3/1979 | Jones et al. ...................... 260/397.2 |

OTHER PUBLICATIONS

J. Chem. Soc. (1976), pp. 731–735.
Tetrahedron Letters, 20 (1977), 1695–1698.
C. R. Acad. Sc., Paris, 285 (1977), 443–446.

*Primary Examiner*—Elbert L. Roberts
*Attorney, Agent, or Firm*—Jon S. Saxe; George M. Gould; John B. Wilson

[57] ABSTRACT

Novel cholestane derivatives, which can be used as intermediates in the manufacture of 25,26-dihydroxy-cholecalciferol, as well as a process for their preparation is described.

5 Claims, No Drawings

CHOLESTANE DERIVATIVES

BACKGROUND OF THE INVENTION

Hydroxy derivatives of vitamin D have commanded particular interest for some time, since a series of such derivatives has been found to be biologically active metabolites. Among these metabolites is 25,26-dihydroxy-cholecalciferol (Biochemistry 9, 4776, 1970). Since these substances are not available from natural sources in large amounts, their synthesis is of particular significance. Several syntheses have been conceived for 25,26-dihydroxy-cholecalciferol [Compt. rend. 285, series D, 443 (1977)]. These syntheses lead to epimer mixtures of 25R- and 25S-compounds, which can be separated only with difficulty. The present invention now provides a novel process which enables 25R,26- and 25S,26-dihydroxy-cholecalciferol to be manufactured also stereoselectively.

DESCRIPTION OF THE INVENTION

One aspect of the present invention is concerned with novel cholestane derivatives of the formula

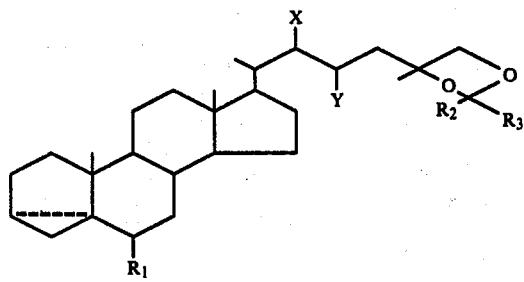

, wherein $R_1$ represents a lower alkoxy group, $R_2$ and $R_3$ each represent a lower alkyl group or $R_2$ and $R_3$ together represent a lower alkylene group, X represents a hydroxy group, a group of the formula $OSO_2R_4$ or a hydrogen atom and Y represents a hydrogen atom or X and Y together represent a carbon-carbon bond and $R_4$ represents a lower alkyl, phenyl or substituted phenyl group, especially cholestane derivatives of the formula

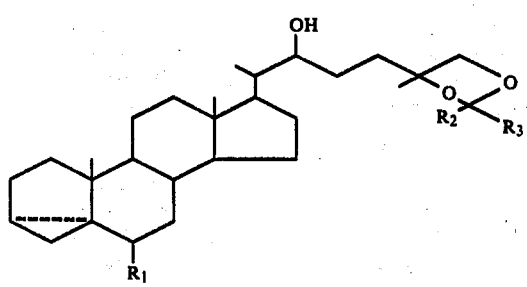

wherein $R_1$, $R_2$ and $R_3$ have the significance given earlier.

A further aspect of the present invention is concerned with a process for the manufacture of 25,26-dihydroxy-cholesterol, which process comprises (a) reacting an i-steroid aldehyde of the formula

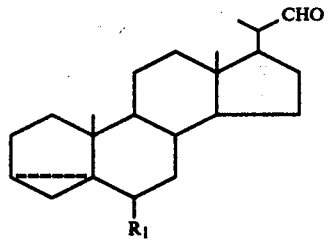

, wherein $R_1$ has the significance given earlier, with a haloketal of the formula

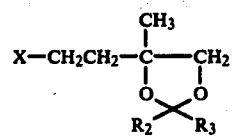

, wherein X represents a chlorine, bromine or iodine atom and $R_2$ and $R_3$ have the significance given earlier, in a Grignard reaction, (b) esterifying the resulting 22-steroid alcohol of the formula

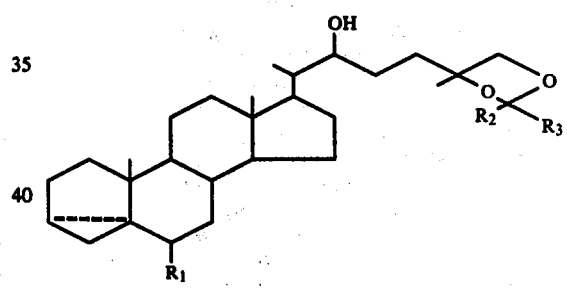

, wherein $R_1$, $R_2$ and $R_3$ have the significance given earlier, with a sulphonic acid, (c) converting the resulting 22-sulphonic acid ester of the formula

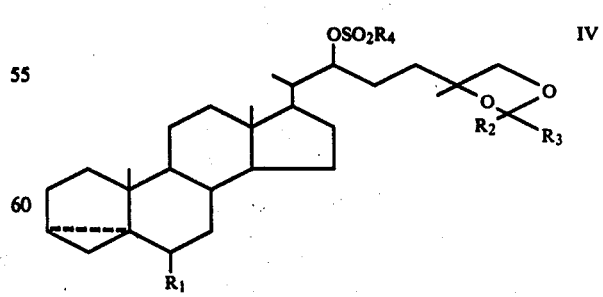

, wherein $R_1$, $R_2$, $R_3$ and $R_4$ have the significance given earlier, into a steroid ketal of the formula

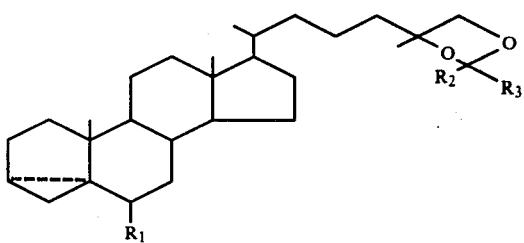

V

, wherein $R_1$, $R_2$ and $R_3$ have the significance given earlier,
either directly by treatment with a complex metal hydride or in two stages by cleavage of the sulphonic acid with formation of a 22,23-double bond and hydrogenation of the resulting steroid ketal of the formula

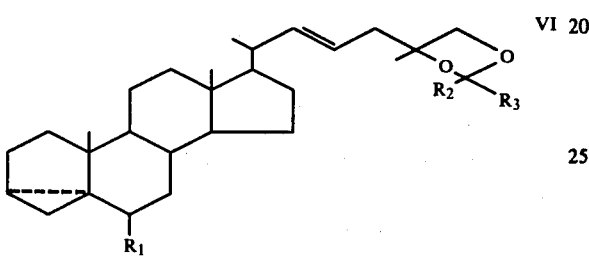

VI

, wherein $R_1$, $R_2$ and $R_3$ have the significance given earlier, (d) subjecting the steroid ketal of formula V to a retro-i-rearrangement and hydrolysing the ketal group.

The Grignard reaction between an i-steroid aldehyde of formula II and a haloketal of formula III can be carried out in a solvent which is customarily used for Grignard reactions (e.g. an ether such as tetrahydrofuran). The reaction is conveniently carried out at a temperature between 0° C. and room temperature. A compound of formula III in which X represents a bromine atom is preferably used. Examples of lower alkyl groups denoted by $R_2$ and $R_3$ are methyl, ethyl and propyl, with methyl being preferred. Examples of alkylene groups denoted by $R_2$ and $R_3$ together are ethylene and propylene. Examples of lower alkoxy groups denoted by $R_1$ are $C_{1-6}$-alkoxy groups, especially methoxy.

The product of the Grignard reaction can be worked-up in the customary manner; for example, by hydrolysis with a weak acid such as aqueous ammonium chloride solution.

In a preferred embodiment of this process, a (20S)-i-steroid aldehyde of formula II is reacted with an optically active compound of formula III or its Grignard compound, especially (4S)-4-(2-bromoethyl)-2,2,4-trimethyl-1,3-dioxolane. When an optically active compound of formula III is used there is obtained a cholestane derivative of formula I having the 25R- or 25S-configuration depending on the chirality which the compound of formula III possesses.

The esterification of the 22-hydroxy group in a steroid of formula I can be carried out by reaction with a reactive sulphonic acid derivative of the formula $R_4SO_2Y$, wherein Y represents a bromine or chlorine atom or a group of the formula $R_4SO_2O-$ and $R_4$ has the significance given earlier, in a suitable organic solvent, preferably in the presence of an acid acceptor. Examples of alkanesulphonic acids are methanesulphonic acid and ethanesulphonic acid, examples of substituted benzenesulphonic acids are lower-alkylbenzenesulphonic acids such as p-toluenesulphonic acid, or p-nitrobenzenesulphonic acid. Suitable organic solvents for the esterification are aromatic solvents such as benzene, toluene, and xylene or hetero-aromatic solvents such as pyridine, picoline or collidine. Examples of acid acceptors which can be used are aliphatic amines such as triethylamine, aromatic amines such as dimethylaniline and hetero-aromatic amines such as pyridine, picoline or collidine. In the latter case, the acid acceptor can simultaneously serve as the solvent.

A sulphonyl ester of formula IV can be converted into a compound of formula V by treatment with a complex metal hydride such as lithium aluminium hydride. This reductive cleavage of the sulphonic acid ester group can be carried out in an inert organic solvent (e.g. an ether such as tetrahydrofuran) while warming, for example up to the reflux temperature of the solvent. In this treatment there can be obtained as a byproduct a compound of formula VI hereinbefore which can be converted into a compound of formula V by catalytic hydrogenation.

Alternatively, a sulphonyl ester of formula IV can be converted into a compound of formula VI which, in turn, can be converted into a compound of formula V by hydrogenation. The cleavage of the sulphonyl ester group from a compound of formula IV with the formation of a compound of formula VI can be carried out by treatment with a base such as N,N-dimethylaniline, pyridine, collidine, or lithium bromide or lithium carbonate, or a mixture of lithium bromide and lithium carbonate. The hydrogenation of a compound of formula VI to give a compound of formula V can be carried out catalytically, for example, in the presence of noble metals such as platinum, palladium or rhodium, or with nickel catalysts.

The retro-i-rearrangement of a steroid of formula V can be carried out by treatment with an acid in a suitable solvolytic medium. As the solvolytic media there come into consideration aqueous media which contain a miscible co-solvent. Suitable co-solvents are ethereal solvents (e.g. tetrahydrofuran or dioxan), ketones (e.g. acetone and methyl ethyl ketone) or alcohols (e.g. ethanol). As the acids there come into consideration mineral acids such as hydrochloric acid, hydrobromic acid or sulphuric acid, or organic sulphonic acids such as benzenesulphonic acid or p-toluenesulphonic acid. When these acids are used the ketal group is simultaneously hydrolysed.

The thus-obtained 25,26-dihydroxy-cholesterol can be converted into 25,26-dihydroxy-cholecalciferol, for example as described in Steroids 24 (1974), page 463. The following Examples illustrate the present invention:

EXAMPLE 1

23 g of S-2-methylbutane-1,2,4-triol-1,2-acetonide (ca 86%) were dissolved in 100 ml of methylene chloride. 38 g of triphenylphosphine were dissolved in this solution and then 23.2 g of N-bromosuccinimide were added at 0° C. within 15 minutes. The mixture was stirred at room temperature for 1 hour, then treated with 300 ml of hexane and filtered through 100 g of silica gel. After washing with hexane, the filtrate was evaporated. There were obtained as the residue 20.9 g of (4S),4-(2-bromoethyl)-2,2,4-trimethyl-1,3-dioxolane in the form of a colourless oil; $[\alpha]_D = +2.89°$ (c=4.1% in chloroform).

EXAMPLE 2

19.2 g of (4S),4-(2-bromoethyl)-2,2,4-trimethyl-1,3-dioxolane were added to a suspension of 2.5 g of magnesium shavings in 100 ml of tetrahydrofuran. The mixture was heated to reflux for 0.5 hour, subsequently cooled to 0° C. and treated with 32 g of (20S)-6β-methoxy-20-methyl-3α,5-cyclo-5α-pregnan-21-al. The mixture was stirred at 0° C. for 3 hours and at room temperature for 15 hours, then treated with 50 ml of saturated ammonium chloride solution and extracted three times with 100 ml of ether. The ethereal extract was dried over magnesium sulphate and evaporated. The residue was chromatographed on silica gel with toluene/ethyl acetate (2:1). There were obtained 20.3 g of (22RS)-6β-methoxy-24-[(S)-2,2,4-trimethyl-1,3-dioxolan-4-yl]-3α,5-cyclo-5α-cholan-22-ol; $[\alpha]_D = +33.4°$ (c=1.7% in chloroform).

EXAMPLE 3

10 g of (22RS)-6β-methoxy-24-[(S)-2,2,4-trimethyl-1,3-dioxolan-4-yl]-3α,5-cyclo-5α-cholan-22-ol were dissolved in 31.4 ml of methanesulphonyl chloride and 179 ml of pyridine. The solution was left to stand overnight, then treated with 400 g of ice and stirred for 1 hour. Thereafter, the mixture was filtered and washed five times with 50 ml of water. The solid substance was dissolved in methylene chloride, the solution was dried over magnesium sulphate and evaporated. There was obtained a crude product which was chromatographed on 300 g of silica gel with toluene/ethyl acetate (2:1). There were obtained 10.3 g of (22RS)-6β-methoxy-24-[(S)-2,2,4-trimethyl-1,3-dioxolan-4-yl]-3β,5-cyclo-22-mesyloxy-5α-cholane of melting point 118°–120° C., $[\alpha]_D = 34.8°$ (c=+2.6% in chloroform).

EXAMPLE 4

10.3 g of (22RS)-6β-methoxy-24-[(S)-2,2,4-trimethyl-1,3-dioxolan-4-yl]-3α,5-cyclo-22-mesyloxy-5α-cholane were dissolved in 100 ml of tetrahydrofuran and the solution was treated with 10.3 g of lithium aluminium hydride. The mixture was heated to reflux for 2 hours, then cooled to 0° C., treated with 60 ml of methanol and subsequently treated dropwise with 60 ml of water. The product was extracted three times with 100 ml of ether, the ethereal phase was dried over magnesium sulphate and evaporated. The residue was taken up in 100 ml of dioxan and shaken in the presence of 4 g of platinum/carbon (10%) for 1 hour under a hydrogen atmosphere. The solution was then filtered and the filtrate was evaporated. There were obtained 7.82 g of (22RS)-6β-methoxy-24-[(S)-2,2,4-trimethyl-1,3-dioxolan-4-yl]-3α,5-cyclo-5α-cholane; $[\alpha]_D = +28.4°$ (c=3.8% in chloroform).

EXAMPLE 5

7.8 g of (22RS)-6β-methoxy-24-[(S)-2,2,4-trimethyl-1,3-dioxolan-4-yl]-3α,5-cyclo-5α-cholane were dissolved in 200 ml of dioxan and, after the addition of 0.3 g of p-toluenesulphonic acid and 60 ml of water, the mixture was heated to reflux for 3 hours. The mixture was then stirred at room temperature for 12 hours and treated with 200 ml of ether. The aqueous phase was washed twice with 50 ml of ether and the combined organic phases were dried over magnesium sulphate and evaporated. The residue was suspended in ether, the suspension was filtered and the residue was washed with ether. After drying the residue, there were obtained 3.6 g of 25S,26-dihydroxy-cholesterol; $[\alpha]_D = -35.8°$ (c=0.4% in methanol).

By treatment of the thus-obtained 25S,26-dihydroxy-cholesterol with acetic anhydride and pyridine there was obtained 25S,26-dihydroxy-cholesterol 3,26-diacetate; $[\alpha]_D = -38.6°$ (c=1.4% in chloroform).

We claim:

1. A cholestane derivative of the formula

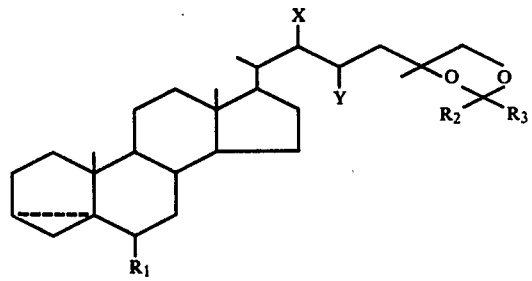

wherein $R_1$ is lower alkoxy, $R_2$ and $R_3$ each independently is lower alkyl or $R_2$ and $R_3$ taken together are lower alkylene, X is hydrogen, hydroxy or —OSO₂R₄ where $R_4$ is lower alkyl, phenyl or substituted phenyl, and Y is hydrogen or X and Y taken together are a carbon-carbon bond.

2. The cholestane derivative of claim 1 wherein X is hydroxy and Y is hydrogen.

3. The compound of claim 2 which is (22RS)-6β-methoxy-24-[(S)-2,2,4-trimethyl-1,3-dioxolan-4-yl]-3α,5-cyclo-5α-cholan-22-ol.

4. The compound of claim 1 which is (22RS)-6β-methoxy-24-[(S)-2,2,4-trimethyl-1,3-dioxolan-4-yl]-3α,5-cyclo-22-mesyloxy-5α-cholane.

5. The compound of claim 1 which is (22RS)-6β-methoxy-24-[(S)-2,2,4-trimethyl-1,3-dioxolan-4-yl]-3α,5-cyclo-5α-cholane.